United States Patent
Esquivel-Upshaw et al.

(10) Patent No.: US 12,364,583 B2
(45) Date of Patent: Jul. 22, 2025

(54) QUARTERNIZED TITANIUM-NITRIDE ANTI-BACTERIAL COATING FOR DENTAL IMPLANTS

(71) Applicant: University of Florida Research Foundation, Inc., Gainesville, FL (US)

(72) Inventors: Josephine F. Esquivel-Upshaw, Gainesville, FL (US); Fan Ren, Gainesville, FL (US); Patrick Carey, Gainesville, FL (US); Arthur E. Clark, Jr., Gainesville, FL (US); Christopher D. Batich, Gainesville, FL (US)

(73) Assignee: University of Florida Research Foundation, INC., Gainesville, FL (US)

(*) Notice: Subject to any disclaimer, the term of this patent is extended or adjusted under 35 U.S.C. 154(b) by 104 days.

(21) Appl. No.: 18/489,926

(22) Filed: Oct. 19, 2023

(65) Prior Publication Data
US 2024/0041575 A1    Feb. 8, 2024

Related U.S. Application Data

(62) Division of application No. 17/258,022, filed as application No. PCT/US2019/044556 on Jul. 31, 2019, now Pat. No. 11,864,964.
(Continued)

(51) Int. Cl.
*A61C 13/083*    (2006.01)
*A61C 8/00*    (2006.01)

(52) U.S. Cl.
CPC ........ *A61C 13/0835* (2013.01); *A61C 8/0013* (2013.01); *A61C 2201/00* (2013.01)

(58) Field of Classification Search
CPC ............ A61C 13/0835; A61C 13/0013; A61C 2201/00; A61L 27/54; A61L 27/10
See application file for complete search history.

(56) References Cited

U.S. PATENT DOCUMENTS

| | | | |
|---|---|---|---|
| 5,573,401 A | * | 11/1996 | Davidson ............. A61C 8/0012 433/201.1 |
| 6,039,940 A | | 3/2000 | Perrault et al. |

(Continued)

FOREIGN PATENT DOCUMENTS

| | | |
|---|---|---|
| CN | 102964766 A | 3/2013 |
| CN | 105343929 A | 2/2016 |

(Continued)

OTHER PUBLICATIONS

Harris et al., Staphylococci and Implant Surfaces: A Review Injury: Infection in Fracture Fixation, Basic Research, to Diagnosis, to Evidence-Based Treatment vol. 37, Issue: 2, pp. S3-S14, May 2006.
(Continued)

*Primary Examiner* — Yogesh P Patel
(74) *Attorney, Agent, or Firm* — Thomas | Horstemeyer LLP.

(57) ABSTRACT

Disclosed herein is a method for forming an anti-microbial layer on an apparatus. Also disclosed is a method for improving the anti-bacterial properties of a titanium device coated with titanium-nitride (TiN). Also disclosed is a medical apparatus comprising an anti-microbial layer prepared by the disclosed methods. This abstract is intended as a scanning tool for purposes of searching in the particular art and is not intended to be limiting of the present disclosure.

11 Claims, 4 Drawing Sheets

Top View

Side View

Related U.S. Application Data

(60) Provisional application No. 62/712,553, filed on Jul. 31, 2018.

(56) References Cited

U.S. PATENT DOCUMENTS

| | | | |
|---|---|---|---|
| 8,591,994 B2* | 11/2013 | Deisenroth | A61L 15/46 427/299 |
| 2010/0178427 A1* | 7/2010 | Deisenroth | A61L 29/16 427/299 |
| 2011/0076387 A1 | 3/2011 | Koehl et al. | |
| 2014/0154297 A1 | 6/2014 | Krongauz et al. | |

FOREIGN PATENT DOCUMENTS

| | | |
|---|---|---|
| JP | 4945743 B2 | 3/2012 |
| WO | 2011038897 A2 | 4/2011 |
| WO | WO-2021137159 A1 | 7/2021 |

OTHER PUBLICATIONS

Campoccia et al., A review of the Biomaterials Technologies for Infection-Resistant Surfaces Biomaterials, vol. 34, Issue: 34, pp. 8533-8554, Nov. 2013.
Pupo et al., An Innovative Quaternary Ammonium Methacrylate Polymer can Provide Improved Antimicrobial Properties for a Dental Adhesive System, Journal of Biomaterials Science, Polymer Edition vol. 24, Issue: 12, pp. 1443-1458, Feb. 18, 2013.
A. Mombelli, N. Müller and N. Cionca, "The epidemiology of peri-implantitis", Clinical Oral Implants Research, vol. 23, pp. 67-76, 2012.
A. Mombelli and N. Cionca, "Systemic diseases affecting osseointegration therapy", Clinical Oral Implants Research, vol. 17, No. 2, pp. 97-103, 2006.
S. Renvert, A. Roos-Jansåker and N. Claffey, "Non-surgical treatment of peri-implant mucositis and peri-implantitis: a literature review", Journal of Clinical Periodontology, vol. 35, pp. 305-315, 2008.
N. Claffey, E. Clarke, I. Polyzois and S. Renvert, "Surgical treatment of peri-implantitis", Journal of Clinical Periodontology, vol. 35, pp. 316-332, 2008.
M. Quirynen, M. Abarca, N. Van Assche, M. Nevins and D. van Steenberghe, "Impact of supportive periodontal therapy and implant surface roughness on implant outcome in patients with a history of periodontitis", Journal of Clinical Periodontology, vol. 34, No. 9, pp. 805-815, 2007.
S. Safii, R. Palmer and R. Wilson, "Risk of Implant Failure and Marginal Bone Loss in Subjects with a History of Periodontitis: A Systematic Review and Meta-Analysis", Clinical Implant Dentistry and Related Research, 2009.
A. Mombelli and N. Lang, "Antimicrobial treatment of peri-implant infections", Clinical Oral Implants Research, vol. 3, No. 4, pp. 162-168, 1992.
N. Claffey and J. Egelberg, "Clinical indicators of probing attachment loss following initial periodontal treatment in advanced periodontitis patients", Journal of Clinical Periodontology, vol. 22, No. 9, pp. 690-696, 1995.
A. Mombelli and F. Décaillet, "The characteristics of biofilms in peri-implant disease", Journal of Clinical Periodontology, vol. 38, pp. 203-213, 2011.
G. Persson and S. Renvert, "Cluster of Bacteria Associated with Peri-Implantitis", Clinical Implant Dentistry and Related Research, vol. 16, No. 6, pp. 783-793, 2013.
A. Mombelli, M. Oosten, E. Schürch and N. Lang, "The microbiota associated with successful or failing osseointegrated titanium implants", Oral Microbiology and Immunology, vol. 2, No. 4, pp. 145-151, 1987.
C. Berry, T. Moore, J. Safar, C. Henry and M. Wagner, "Antibacterial Activity of Dental Implant Metals", Implant Dentistry, vol. 1, No. 1, p. 59, 1992.
R. van Hove, I. Sierevelt, B. van Royen and p. Nolte, "Titanium-Nitride Coating of Orthopaedic Implants: A Review of the Literature", BioMed Research International, vol. 2015, pp. 1-9, 2015.
X. Li, P. Gao, P. Wan, Y. Pei, L. Shi, B. Fan, C. Shen, X. Xiao, K. Yang and Z. Guo, "Novel Bio-functional Magnesium Coating on Porous Ti6Al4V Orthopaedic Implants: In vitro and In vivo Study", Scientific Reports, vol. 7, p. 40755, 2017.
F. Khosravi and H. Mansouri-Torshizi, "Antibacterial combination therapy using Co3+, Cu2+, Zn2+ and Pd2+ complexes: Their calf thymus DNA binding studies", Journal of Biomolecular Structure and Dynamics, vol. 36, No. 2, pp. 512-531, 2017.
G. Li, Q. Zhao, H. Yang and L. Cheng, "Antibacterial and Microstructure Properties of Titanium Surfaces Modified with Ag-Incorporated Nanotube Arrays", Materials Research, vol. 19, No. 3, pp. 735-740, 2016.
S. Mei, H. Wang, W. Wang, L. Tong, H. Pan, C. Ruan, Q. Ma, M. Liu, H. Yang, L. Zhang, Y. Cheng, Y. Zhang, L. Zhao and P. Chu, "Antibacterial effects and biocompatibility of titanium surfaces with graded silver incorporation in titania nanotubes", Biomaterials, vol. 35, No. 14, pp. 4255-4265, 2014.
Y. Xue, H. Xiao and Y. Zhang, "Antimicrobial Polymeric Materials with Quaternary Ammonium and Phosphonium Salts", International Journal of Molecular Sciences, vol. 16, No. 2, pp. 3626-3655, 2015.
L. Timofeeva and N. Kleshcheva, "Antimicrobial polymers: mechanism of action, factors of activity, and applications", Applied Microbiology and Biotechnology, vol. 89, No. 3, pp. 475-492, 2010.
M. Hassan and H. Ibrahim, "Characterization and antimicrobial properties of metal complexes of polypropylene fibers grafted with acrylic acid using gamma irradiation", Polymers for Advanced Technologies, vol. 27, No. 4, pp. 532-541, 2015.
J. Oosterhof, K. Buijssen, H. Busscher, B. van der Laan and H. van der Mei, "Effects of Quaternary Ammonium Silane Coatings on Mixed Fungal and Bacterial Biofilms on Tracheoesophageal Shunt Prostheses", Applied and Environmental Microbiology, vol. 72, No. 5, pp. 3673-3677, 2006.
M. Smith and J. March, March's Advanced Organic Chemistry: Reactions, Mechanisms, and Structure, 6th ed. Hoboken, N.J.: Wiley, 2007, p. 555.
M. Harfenist, "The Rate of Quaternization of a Piperazine by Some Propargylic and Allylic Bromides", Journal of the American Chemical Society, vol. 79, No. 16, pp. 4356-4358, 1957.
K. Stanger, J. Lee and B. Smith, "Dramatic Acceleration of the Menschutkin Reaction and Distortion of Halide Leaving-Group Order", The Journal of Organic Chemistry, vol. 72, No. 25, pp. 9663-9668, 2007.
N. Menschutkin, "Über die Affinitätskoeffizienten der Alkylhaloide und der Amine", Zeitschrift für Physikalische Chemie, vol. 6, No. 1, 1890.
J. Lindhe and J. Meyle, "Peri-implant diseases: Consensus Report of the Sixth European Workshop on Periodontology", Journal of Clinical Periodontology, vol. 35, pp. 282-285, 2008.
J. Prathapachandran and N. Suresh, "Management of peri-implantitis", Dental Research Journal, vol. 9, No. 5, p. 516, 2012.
R. Teles, "Peri-implantitis—absence of evidence to support specific treatment protocols", Evidence-Based Dentistry, vol. 4, No. 4, pp. 88-88, 2003.
International Search Report and Written Opinion for PCT/US2019/044556 of Oct. 22, 2019.
EP Search Report; EP Application No. 19843243.7; mailed Mar. 24, 2022 (8Pages).
Ruud P. van Hove,Titanium-Nitride Coating of Orthopaedic Implants: Apr. 20, 2015 (vol. 2015, 10 Pages).

* cited by examiner

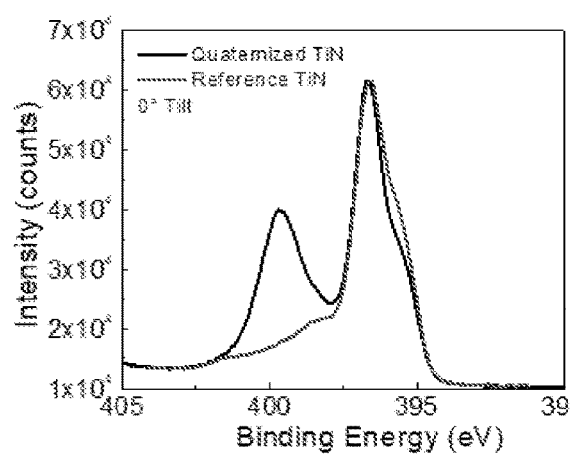
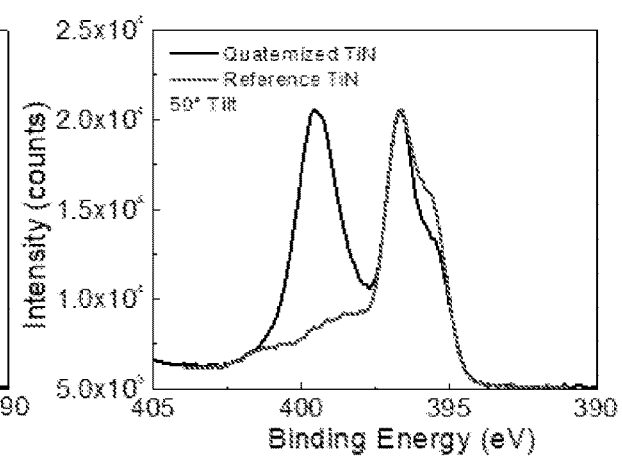
FIG. 3A  FIG. 3B

QUARTERNIZED TITANIUM-NITRIDE ANTI-BACTERIAL COATING FOR DENTAL IMPLANTS

CROSS-REFERENCE TO RELATED APPLICATIONS

This application is a divisional of U.S. patent application Ser. No. 17/258,022, having the title "QUARTERNIZED TITANIUM-NITRIDE ANTI-BACTERIAL COATING FOR DENTAL IMPLANTS", filed on Jan. 5, 2021, which is the 35 U.S.C. § 371 national stage application of PCT Application No. PCT/US2019/044556, filed Jul. 31, 2019, where the PCT claims priority to, and the benefit of, U.S. provisional application entitled "QUARTERNIZED TITANIUM-NITRIDE ANTI-BACTERIAL COATING FOR DENTAL IMPLANTS" having Ser. No. 62/712,553, filed Jul. 31, 2018, all of which are herein incorporated by reference in their entireties.

STATEMENT REGARDING FEDERALLY SPONSORED RESEARCH

This invention was made with government support under DE025001 awarded by the National Institutes of Health. The government has certain rights in this invention.

BACKGROUND

Approximately 5% of all dental implants anchored by osseointegration will fail within 10 years (Mombelli A., et al., Clin Oral Implants Res. 2012 23:67-76; Lindhe J., et al., J Clin Periodontol. 2008 35:282-285; Mombelli A., et al. Clin Oral Implants Res. 2006 17(2):97-103). Implant survival is not well characterized as a function of lifestyle; explorations into patients' past dental history and other medical conditions have provided little in predicating variables. Patients with previous history of periodontal disease have lower implant survival rates, but diseases such as osteoporosis or diabetes gave no clear impact consistently (Mombelli A., et al. Clin Oral Implants Res. 2006 17(2): 97-103; Safii S., et al. Clin Implant Dent Relat Res. 2010 12(3):165-74).

A primary culprit for implant failure is peri-implantitis, which is site specific bacterial infection, which leads to bone loss around the implant and soft tissue inflammation. This definition assumes that there was successful osseointegraiton of the implant initially, thus the disease is degenerative, which excludes implant failure due to infection during the implantation procedure or mechanical failure of the implant. Peri-implantitis has no conclusive treatment to stop infection and progression of the disease, thus prevention of the disease at the earliest of stages is of upmost importance to extend implant lifetime (Prathapachandran J., et al. Dent Res J (Isfahan). 2012 9(5):516-21; Teles R., et al. Evidence-Based Dentistry 2003 4(4):88-88; Renvert S., et al. J Clin Periodontol. 2008 35(8 Suppl):305-15; Claffey, N., et al. J Clin Periodontol. 2008 35(8 Suppl):316-32; Quirynen M., et al. J Clin Periodontol. 2007 34(9):805-15; Mombelli A., et al. Clin Oral Implants Res. 1992 3(4):162-8; Claffey N., et al. J Clin Periodontol. 1995 22(9):690-6). The infection site's bacterial flora has been explored to find if a prevalence of certain bacteria may lend to formation of peri-implantitis. The sub-gingival flora of sites with peri-implantitis have similar flora to that of periodontitis with the majority of bacteria being Gram negative (Mombelli A., et al. J Clin Periodontol. 2011 38 Suppl 11:203-13; Persson G R., et al. Clin Implant Dent Relat Res. 2014 16(6):783-93; Mombelli A., et al. Oral Microbiol Immunol. 1987 2(4):145-51). Persson et al. identified 19 bacterial species with higher counts at the site of peri-implantitis infection than at implant sites without infection, with 7 bacteria strains accounting for 30% of bacterial flora at the infection site as compared to 14% at non-infected implants (Persson G R., et al. Clin Implant Dent Relat Res. 2014 16(6):783-93).

Despite advances in dental research, there is still a scarcity of materials, and methods for preparation of same, for dental implants that provide for sustained and effective inhibition of peri-implantitis. These needs and other needs are satisfied by the present disclosure.

SUMMARY

In accordance with the purpose(s) of the disclosure, as embodied and broadly described herein, the disclosure, in one aspect, relates to methods of preparing antibacterial coatings comprising a quanternized titanium nitride layer. The disclosed antibacterial quaternized TiN surfaces provide a method for improving implant lifetime.

Disclosed herein are methods for forming an antibacterial quaternized TiN surface. In various aspects, the disclosed method comprises reaction of the titanium-nitride (TiN) layer with an alkylating agent, e.g., an allyl halide, to quaternize the titanium-nitride (TiN). For example, in some aspects the allyl halide, e.g. comprises allyl chloride, allyl bromide or ally iodine. The disclosed method can further comprise forming a titanium (Ti) layer, e.g., using rf-magnetron sputtering; formation of a titanium-nitride (TiN) vapor that coats the titanium (Ti) layer with a titanium-nitride (TiN), e.g., using chemical vapor deposition, plasma spray or rf-magnetron sputtering; and then quaternization of the TiN surface using an allyl halide.

Also disclosed is a method for improving the anti-bacterial properties of a dental implant device, e.g., a dental implant device comprising a titanium layer that is coated with titanium-nitride (TiN), comprising reacting the nitride (TiN) layer with an alkylating agent, e.g., an allyl halide such as allyl bromide.

Also disclosed is a medical apparatus comprising an anti-microbial layer prepared by the disclosed methods.

Also disclosed is a medical apparatus, comprising a titanium layer coated with titanium nitride treated with an alkyl halide, such as allyl bromide. For example, in some aspects, the apparatus is a dental prosthesis, or medical prosthesis or any implantable device that utilizes titanium. Therefore, in some aspects, the apparatus further comprises a porcelain layer or Ti bonded to the TiN layer. For example, the porcelain layer can be part of a veneer for a tooth or Ti implants.

Also disclosed is a medical apparatus comprising a titanium layer coated with a titanium nitride layer, wherein the titanium nitride layer further comprises an alkyl halide or alkenyl halide derivative. In some aspects, the alkyl halide derivative is a derivative of a C1-C6 alkyl halide. In some aspects, the alkyl halide derivative is a derivative of a C1-C6 alkenyl halide. In some aspects, the C1-C6 alkenyl halide is allyl bromide. In some aspects, the alkyl halide or alkenyl halide derivative is a quaternary ammonium moiety.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 3A and 3B shows high resolution nitrogen 1s XPS spectra acquired with 0° and 50° tilted with respect of normal direction of TiN and quaternized TiN surface.

Figure 1:
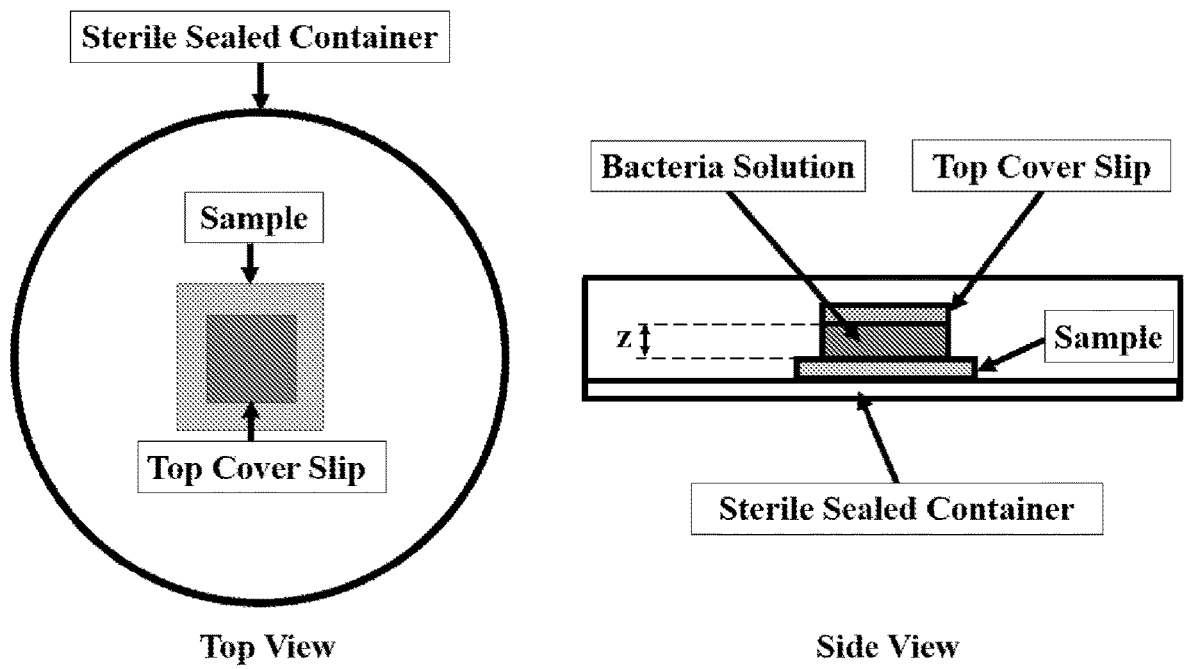
FIG. 1 shows a top and side view of bacterial incubation on sample surfaces for defined film thickness.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

Aspects of the present disclosure will employ, unless otherwise indicated, techniques of chemistry, biology, and the like, which are within the skill of the art.

Before the aspects of the present disclosure are described in detail, it is to be understood that, unless otherwise indicated, the present disclosure is not limited to particular materials, reagents, reaction materials, manufacturing processes, or the like, as such can vary.

It is also to be understood that the terminology used herein is for purposes of describing particular aspects only, and is not intended to be limiting. It is also possible in the present disclosure that steps can be executed in different sequence where this is logically possible.

A number of aspects of the invention have been described. Nevertheless, it will be understood that various modifications may be made without departing from the spirit and scope of the invention. Accordingly, other aspects are within the scope of the following claims.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "an implant," "a layer," or "a biofilm," includes, but is not limited to, two or more such implants, layers, or biofilms, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a quaternized TiN substrate refers to an amount that is sufficient to achieve the desired improvement in the property modulated by the formulation component, e.g. achieving the desired level of biofilm inhibition. The specific level in terms of quaternization of TiN in a composition required as an effective amount will depend upon a variety of factors including the amount and type of modifying agent used, thickness of a TiN layer, implant type, and end use of the article made using the composition.

As used herein, the terms "allylic halide" or "allyl halide" refers to an alkyl halide in wherein a carbon atom next to a double bonded carbon atom comprises one or more halogen atoms.

As used herein, the terms "optional" or "optionally" means that the subsequently described event or circumstance can or cannot occur, and that the description includes instances where said event or circumstance occurs and instances where it does not.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

B. Disclosed Quaternized Antibacterial Coatings

Disclosed herein are antibacterial coatings prepared using the disclosed methods. In various aspects, the disclosed antibacterial coatings comprise a titanium nitride (TiN) layer comprising quaternization of surface moieties, i.e., an antibacterial quaternized TiN surface. In various aspects, the quaternized antibacterial coatings having an increased positive charge compared to TiN coated implants not treated using the disclosed methods.

Use of antibacterial coatings may provide a method for improving implant lifetime. Even use of different metals in an implant has significant effect on bacterial growth. Titanium-nitride (TiN) is the most promising metal as it promotes osseointegration while also having lower bacterial growth rate than traditional titanium implants (Berry C W., et al. Implant Dent. 1992 1(1):59-65; van Hove R P., et al. Biomed Res Int. 2015 2015:485975). Current implants make use of TiN plasma spray coatings on titanium, coatings are on the order of several microns thick; however, peri-implantitis is still a problem with these implants. Many groups have explored addition of charged metallic particles to the implant (copper, silver, magnesium, etc.) however a concern with all these implants is out diffusion of these ions to the surrounding tissue (Li X., et al. Sci Rep. 2017 7:40755; Khosravi F., et al. J Biomol Struct Dyn. 2018 36(2):512-531; Li G., et al. Materials Res. 2016 19(3):735-740; Mei S., et al. Biomaterials. 2014 35(14):4255-65).

To avoid concerns of charged metallic species undergoing unfavorable interactions with the surrounding tissues, a method of producing a quaternary nitrogen on the TiN surface was identified. Nitrogen atom disrupts the cell wall, leading to leakage of the cell contents and eventual apoptosis of the bacteria (Xue Y., et al. Int J Mol Sci. 2015 16(2):3626-55; Timofeeva L., et al. Appl Microbiol Biotechnol. 2011 89(3):475-92; Khosravi F., et al. J Biomol Struct Dyn. 2018 36(2):512-531; Hassan M., et al. Polym Adv Technol. 2015 27(4):532-541; Oosterhof J., et al. Appl Environ Microbiol. 2006 72(5):3673-7).

In various aspects, the disclosed quaternized antibacterial coatings comprise a titanium layer having a thickness of about 100 Å to about 3000 Å and a titanium nitride layer thereon having a thickness of about 50 Å to about 1000 Å, wherein the titanium nitride comprises a quaternized modification via the disclosed methods herein, i.e., quaternization of nitrogen moieties in the titanium nitride layer via an alkylation reaction, such as Menschutkin reaction using an alkylating agent such as an alkyl halide, e.g., an allyl halide.

In a further aspect, the titanium layer has a thickness of about 100 Å, about 150 Å, about 200 Å, about 250 Å, about 300 Å, about 350 Å, about 400 Å, about 450 Å, about 500 Å, about 550 Å, about 600 Å, about 650 Å, about 700 Å, about 750 Å, about 800 Å, about 850 Å, about 900 Å, about 950 Å, about 1000 Å, about 1050 Å, about 1100 Å, about 1150 Å, about 1200 Å, about 1250 Å, about 1300 Å, about 1350 Å, about 1400 Å, about 1450 Å, about 1500 Å, about 1550 Å, about 1600 Å, about 1650 Å, about 1700 Å, about 1750 Å, about 1800 Å, about 1850 Å, about 1900 Å, about 1950 Å, about 2000 Å, about 2050 Å, about 2100 Å, about 2150 Å, about 2200 Å, about 2250 Å, about 2300 Å, about 2350 Å, about 2400 Å, about 2450 Å, about 2500 Å, about 2550 Å, about 2600 Å, about 2650 Å, about 2700 Å, about 2750 Å, about 2800 Å, about 2850 Å, about 2900 Å, about 2950 Å, about 3000 Å; or any range encompassed by the foregoing values; or any combination of the foregoing values.

In a further aspect, the titanium nitride layer has a thickness of about 50 Å, about 100 Å, about 150 Å, about 200 Å, about 250 Å, about 300 Å, about 350 Å, about 400 Å, about 450 Å, about 500 Å, about 550 Å, about 600 Å, about 650 Å, about 700 Å, about 750 Å, about 800 Å, about 850 Å, about 900 Å, about 950 Å, about 1000 Å; or any range encompassed by the foregoing values; or any combination of the foregoing values.

C. Disclosed Methods of Preparing Quaternized Antibacterial Coatings

Disclosed herein is a method for forming an anti-microbial layer that involves first forming a titanium (Ti) vapor that solidifies to form a titanium (Ti) layer. The method then involves forming a titanium-nitride (TiN) vapor that coats the titanium (Ti) layer with a titanium-nitride (TiN) layer with evaporation, chemical vapor deposition, plasma spray or sputtering. Finally, the method involves reacting the titanium-nitride (TiN) layer with an alkylating agent, e.g., an alkyl halide to quaternize the titanium-nitride (TiN). For example, in some aspects the alkylating agent can be an allyl halide, e.g., comprising, but not limited to, an allyl chloride, allyl bromide or ally iodine. In various aspects, the quaternization of nitrogen moieties in the titanium nitride layer comprises a Menschutkin reaction utilizing an aforementioned alkylating agent.

The antibacterial efficiency of the disclosed quaternized antibacterial coatings can be tested through standard methodology, e.g., ISO 22196 for the measurement of antibacterial activity on a surface. Confirmation of surface chemistry change conferred using the disclosed methods can be assessed via Sessile drop contact angle and X-Ray Photoelectron Spectroscopy.

D. Disclosed Dental Implants

In various aspects, the disclosed quaternized antibacterial coatings provide resistance to bacterial or microbial growth on an implant, e.g., a dental implant. For example, the disclosed quaternized antibacterial coatings reduce biofilm formation by at least 10% compared to a compositionally similar titanium nitride coating that is not modified by the disclosed methods to comprise a disclosed quaternized antibacterial coating, in particular the reduction in biofilm is observable within four hours using the methods disclosed herein. In a still further aspect, the reduction in biofilm formation on a disclosed quaternized antibacterial coating compared to a compositionally similar titanium nitride coating that is not modified using the disclosed is a reduction within about four hours of about 10%, about 15%, about 20%, about 25%, about 30%, about 35%, about 40%, about 45%, about 50%, about 55%, about 60%, about 65%, about 70%, about 75%; or any range encompassed by the foregoing values; or any combination of the foregoing values.

In various aspects, a disclosed dental component can be a dental implant, dental component is selected from the group consisting of a dental implant, crown, bridge, filling, veneer, inlay, onlay, endodontic device, or orthodontic bracket. In a particular aspect, the dental component is a dental implant. The dental component can be porcelain, ceramic, resin, or a combination thereof comprising a titanium layer upon which is a titanium nitride layer comprising a disclosed quaternized antibacterial coating.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Antibacterial Properties of Charged TiN Implant Surfaces for Dental Implants Materials and Method Titanium. The starting substrate were 1 inch by 1 inch cover glasses. Cover glasses were cleaned with acetone, isopropanol (IPA) and dilute HCl (10% in deionized (DI) water). To simulate the Ti implant, 100 nm of high purity Ti (0.9999) was deposited on the cover glass surface by electron beam evaporation at a pressure of 8×10-7 Torr. Prior to biofilm growth the Ti samples were rinsed with the following solvent sequence: acetone, IPA, and DI water. Upon exposure to ambient, low quality native oxides are present on all Ti surface. The native oxides were removed by sonicating the samples in 1:10 HCl:DI water, then treating with hydrogen peroxide at 60° C. to grow a high quality oxide layer. Contact angle was used to verify consistent samples surfaces from batch to batch.

Titanium Nitride. 1 inch by 1 inch cover glasses were also used for preparing for TiN substrates, and cover glasses were cleaned with acetone, IPA and dilute HCl. 1000 Å titanium was first deposited by rf-magnetron sputtering at a deposition pressure of 5 mTorr in Ar ambient on cover glasses. The Ti base layer was employed to simulate a Ti implant being plasma spray coated with titanium nitride. Without removing the sample from the chamber, 500 Å of TiN was subsequently deposited by rf-magnetron sputtering with a TiN target at room temperature in a pure Ar ambient. The platen for holding the samples was biased at 30-40 V to improve uniformity and stoichiometry of deposited TiN layer. Prior to biofilm growth the TiN samples were rinsed with the following solvent sequence: acetone, IPA, and DI water. Then, the sample was sonicated in 1:10 of HCl: DI water. Contact angle was used to verify consistent samples surfaces from batch to batch.

Quaternized Titanium Nitride. Quaternized TiN substrates were prepared by converting nitrogen atoms on TiN surface into quaternary nitrogen by submerging the TiN substrates in an acetonitrile and allyl bromide solution for 1 hour to quaternize the surface. After quaternization, an IPA and DI water rinse were used to remove any excess solvent and reagent. Contact angle measurements were used to verify consistent samples surfaces from batch to batch.

Biofilm Incubation and Testing. All bacteria work used sterilized materials and was performed under flame to prevent any cross contamination from outside sources. Samples were autoclaved at 125° C. for 20 minutes immediately prior to growth and were kept in sealed containers until removed.

On the day of testing, a paper point was used to extract subgingival bacteria between the lower last premolar and first molar from the patient. The paper point was placed in Ringer solution to suspend and preserve the bacteria. To remove the bacteria from the paper point, the sample was vortexed and sonicated, then vortexed again prior to any removal of bacteria containing solution from the container.

Each sample to be tested for bacteria growth was placed in an individual sterile container. Bacteria solution was micropipetted on to the surface to form film thicknesses (z-height) of 75, 100 and 125 µm, see FIG. 1 for diagram. The samples were incubated in a Bactron 300 anaerobic chamber in a dark box for 4 hours. 4 hours was chosen to be tested as it provided significant quantifiable differences in bacteria growth between the samples. Post incubation the bacteria solution was removed from the sample surface by sonicating and vortexing in fresh Ringer solution. The resulting Ringer solution was further diluted and plated on Tryptic Soy Agar and allowed to grow under anaerobic conditions for 48 hours. Subsequently, the plates were removed and colony forming units counted to evaluate antibacterial efficiency of the quaternized sample as compared to reference Titanium and Titanium Nitride samples.

Confirmation of Surface Reaction. The successful integration and longevity of a dental implant requires the interface between bone and implant remain bacteria free. TiN has been shown to greatly improve development of bone around an implant and decrease the bacteria count over Ti implants. With this next step in antibacterial TiN, the longevity and survival percent of implants will improve.

To confirm a successful Menschutkin surface reaction of the TiN implant with the reagent, Sessile contact angle measurement was used, see Table 1. The TiN sample was measured to be very hydrophilic after deposition and cleaning, due to the high ability for hydrogen bonding of the water droplet to the nitrogen rich surface. The Titanium sample after treatment with hydrogen peroxide is expected to be very hydrophilic due to the high quantity of Ti—OH and Ti=O bonds present. The cleaning treatments that were developed for each surface was in part to ensure that a highly reproducible surface could be created and give the low variance in contact angle that is reported.

TABLE 1

Contact angle measurement of quaternized surface demonstrates distinct shift and reaction saturation within an hour

| Sample | Contact Angle (°) |
|---|---|
| Titanium after $H_2O_2$ clean | 12 ± 2 |
| TiN after clean | <6 |
| TiN in solvent 120 min (no reagent) | 16 ± 2 |
| TiN Quaternization 30 minutes | 67 ± 1 |
| TiN Quaternization 60 minutes | 72 ± 3 |
| TiN Quaternization 120 minutes | 71 ± 2 |

With the quaternized TiN surface, prior to measurement the contact angle is difficult to predict as the surface does become charged with the quaternized nitrogen lending to potential hydrophilicity; however, the carbon chain from the allyl group extends from the surface lending to the potential hydrophobicity. A reference TiN sample was soaked in the solvent to ensure any changes related to the acetonitrile could be accounted for and not be mistaken for a surface reaction. From Table 1, the reaction produced a contact angle of ~72°, distinct from all other disk types and the control in solvent (22°). Menschutkin reactions are known to progress very rapidly, evident by the reaction saturating within an hour. Of note, the allylic halide will react quicker with higher substituted amines, due to the lower enthalpy of formation, hence the Menschutkin reaction is well suited for formation of quaternary ammonium salts and is difficult to stop at secondary or tertiary products (Harfenist M., et al. J Am Chem Soc 1957 79(16):4356-4358; Stanger K., et al. J Org Chem. 2007 72(25):9663-8; Menschutkin N. Zeitschrift für Physikalische Chemie. 1890 6(1)).

Figure 2:
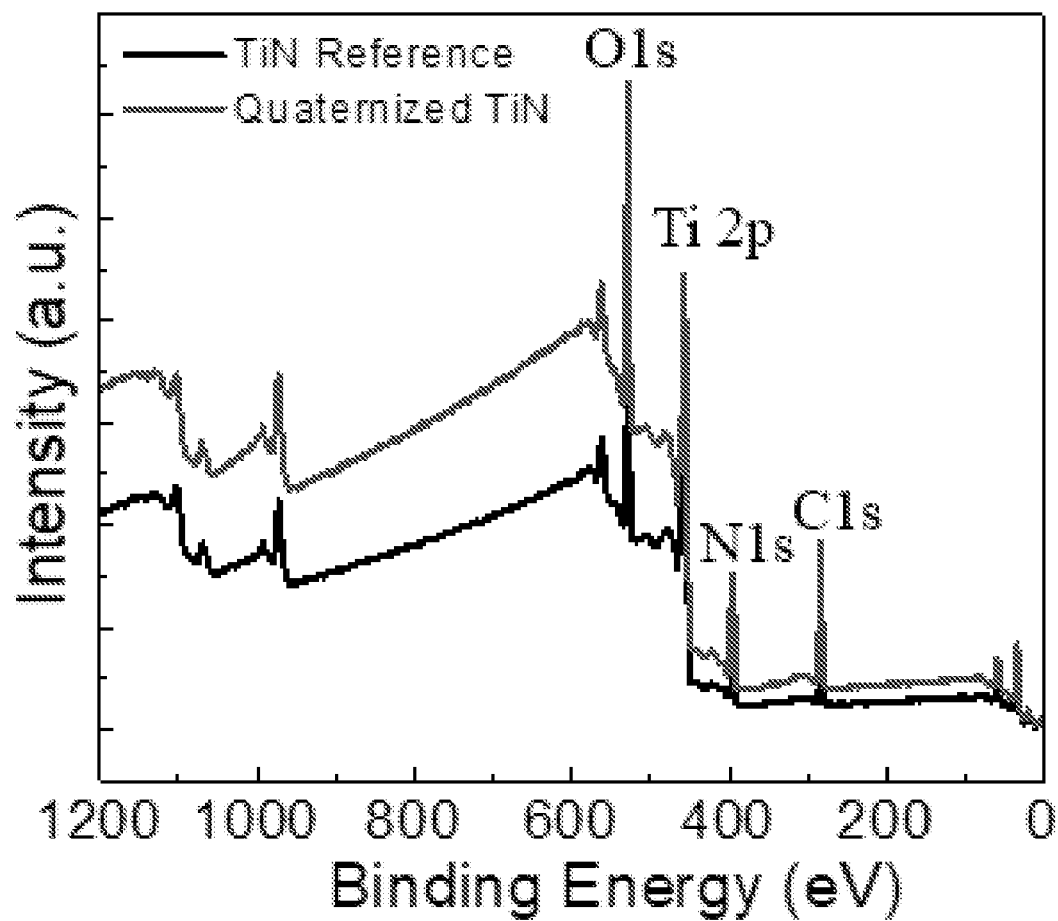
FIG. 2 shows stacked wide range XPS survey scan of TiN and quaternized TiN sample.

To further confirm and identify change in surface chemistry XPS was performed. XPS surface analysis was employ to further confirm and identify changes in surface chemistry of quaternized TiN surface. As shown in FIG. 2, the wide range analyzes were acquired from the surface of the TiN and quaternized TiN substrates and Ti, O, N and C were the only elements identified on these two samples; indicating the general surface chemistry of TiN and quaternized TiN samples were identical. Therefore, a detailed peak analysis is necessary for confirmation of the surface reaction. High resolution XPS spectra of the N 1s regions acquired at 0 and 50° angle with respect to the normal for the TiN and quaternized TiN surface, as shown in FIGS. 3a and 3b, respectively. The main N peak corresponding to Ti—N bonds located at 396.75 eV and there was an N satellite peak at 398.48 eV. The shoulder peak of N for Ti—N at 394.5 eV was resultant of N on N—Ti—O. The XPS peak for quaternized nitrogen bound to ethyl group ($-CH_2CH_3$), $N^+$, was 399.75 eV. As compared to the 0° spectra, surface effects were more pronounced for the spectra taken 50° tilted, and the penetration depth of the x-ray source was greatly reduced. For the N spectra of TiN substrate, the peak corresponding to the N of N—Ti—O was more pronounced due to the oxide presence on the TiN surface. For the N 1s spectra of the quaternized nitrogen, this effect was evident in the increased relative intensity of the quaternized nitrogen peak at 399.75 eV to the TiN peak at 396.5 eV, at 50°; indicating the $N^+$ atoms situated on the surface of quaternized TiN. In addition, after a gentle sputtering with 500 eV Ar ions for 30 seconds to remove the top atomic layers of the quaternized TiN substrate.

Impact of Quaternized TiN Surface on Biofilm Growth. As previously discussed, the oral microbiome is incredibly diverse, and no singular bacteria has been pinpointed as the root cause of peri-implantitis. Thus, preventing all types of microbial growth near the implant site may provide the best avenue for implant survival. Variance between every run is also expected as each patient's flora will vary day-to-day and may respond differently depending on environmental factors such as diet and hygiene.

Figure 4:
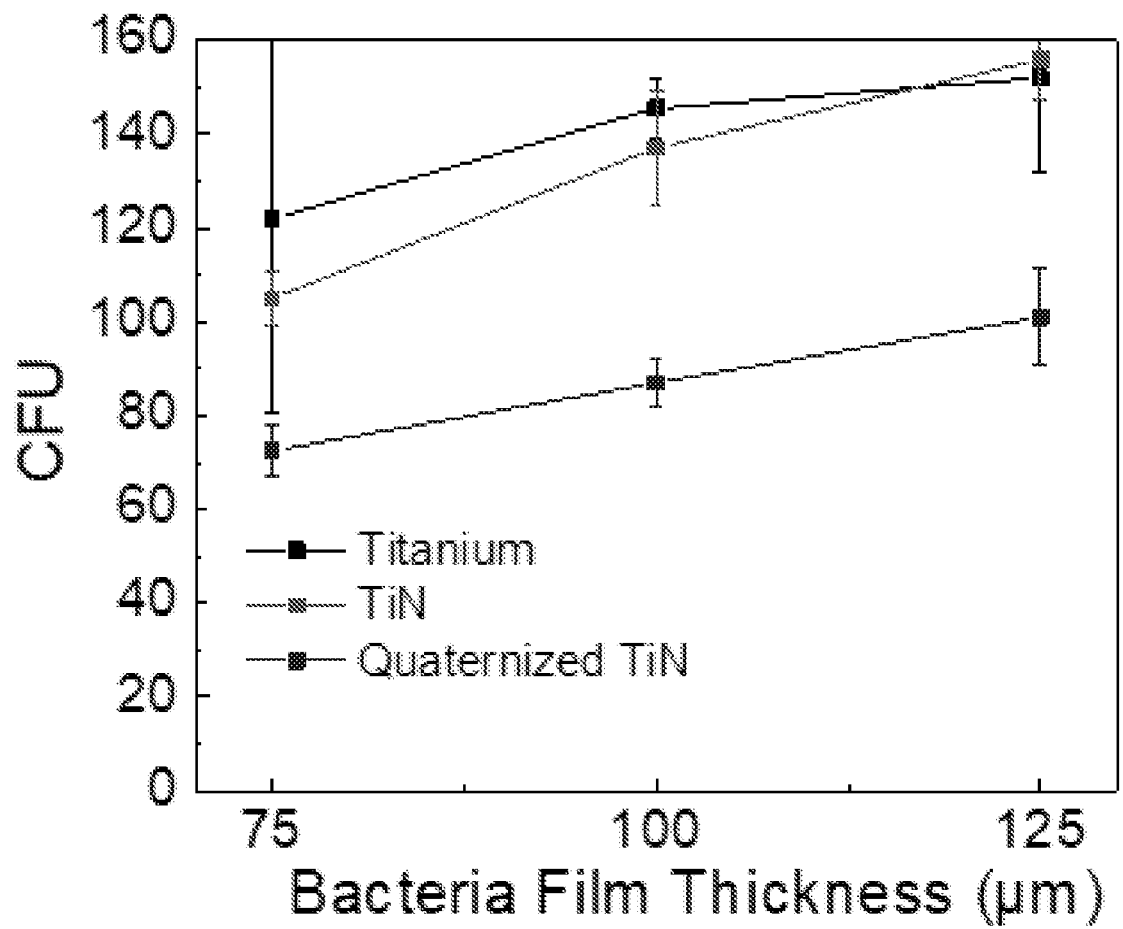
FIG. 4 shows colony forming unit (CFU) of bacteria growth on Ti, TiN or quaternized TiN substrate with different thicknesses of bacterial solution kept between the cover glass slip and Ti, TiN or quaternized TiN substrate.

FIG. 4 shows bacteria growth result of colony forming unit (CFU) with different thicknesses of bacterial solution kept between the cover glass slip and Ti, TiN or quaternized TiN. The antibacterial mechanism of quaternized nitrogen has been proposed to interact with the cell wall, destroy the cytoplasmic membrane leading the leakage of intracellular components and consequent cell death. The quaternized surface outperformed the both the traditional TiN and titanium implants significantly within the short four hour testing period for bacteria film thickness of 75 μm. Even with thick bacteria films that are 125 μm thick, the quaternized surfaces still significantly outperforms the other two substrates indicating that the surface has the ability to neutralize bacteria many microns away. The surface must have this ability to effect bacteria at a distance, as the implant will be surrounded initially by saliva/soft tissue until full osseointegration is complete. Additionally, failure of an implant will be induced by an infection beginning near the soft tissue which will propagate downward towards the base of the implant. However, with the quaternized surface that propagation can be hindered or completely prevented.

The disclosed methods provide a method to convert the surface nitrogen of a TiN coated implant from neutral to positively charged. As discussed herein above, the surface change was monitored and confirmed by Sessile contact angle and XPS measurements. Biofilm growth noted a 40-50% reduction in bacteria over traditional implant surfaces within 4 hours and noticeable effects many microns away. Considering current technology and other works pursuing high biocidal activity for implant structures, this methodology provides a simple method that would require little manufacturing line changes to accommodate and bring to market.

Example 2: Antibacterial Properties of A Disclosed TiN Implant Surfaces for Dental Implants As discussed herein above, the disclosed methods improve the antiseptic properties of a dental implant without using charged metallic ions via conversion of the nitrogen moieties in titanium nitride surface to a positively charged quaternary ammonium via a Menschutkin reaction.

To prepare the antibacterial quaternized TiN surface, an implant which has been coated with TiN was used. The implant was cleaned to improve yield. The implant was washed with two solvents in sequence, acetone and isopropanol, to remove any dust particulate and other residue. The native oxide layer was removed by sonicating in 1:10 HCl:deionized water for 1 minute. This treatment additionally removes any residue that may not have been removed by the solvents. Acetonitrile was used as the solvent; however, any solvent may be used with preference for polar solvents giving improved reaction times (Stanger K., et al. J Org Chem. 2007 72(25):9663-8; Harfenist M., et al. J Am Chem Soc 1957 79(16):4356-4358). An excess of allyl bromide was added to the solvent and continuously stirred. The sample was then submerged in the solution, and full reaction of the surface occurred within about 60 minutes, as confirmed by contact angle measurement. A reference was also measured by submerging in solvent for the duration with no reactant to ensure any changes in surface properties was due to the quaternization.

TABLE 2

| Sample | Contact Angle (°) |
|---|---|
| As-deposited TiN | <6 |
| In solvent 2 hrs (no reaction) | 16 ± 2 |
| Allyl bromide 30 minutes | 67 ± 1 |
| Allyl bromide 60 minutes | 72 ± 3 |
| Allyl bromide 120 minutes | 71 ± 2 |

Without wishing to be bound by a particular theory, the increased hydrophobicity of the treated surfaces can be due to the presence of the allyl groups on the surface which will impart some hydrophobicity. The contact angle measurements provide information on whether or not a reaction has occurred and whether it has saturated.

The biocidal activity was tested using live bacteria cultures from a patient's mouth, which provides the full flora to act against rather than targeting an individual strain of bacteria. The bacteria was incubated on the sample surface using several bacteria film thicknesses. The thickness is defined by keeping the same interaction surface area while varying the volume of bacteria solution added. Across two separate patients and several separate growths, within 4 hours 40-50% reduction in bacteria unit counts were observed for quaternized TiN as compared to traditional Titanium implants, outperforming traditional TiN coatings. FIG. 4 shows for two separate patients a set of typical bacteria growth result of the quaternized samples. The exact efficiency varies, as each patient has different flora which varies depending on environmental factors such as hygiene, diet, and familial history.

Unless defined otherwise, all technical and scientific terms used herein have the same meanings as commonly understood by one of skill in the art to which the disclosed invention belongs. Publications cited herein and the materials for which they are cited are specifically incorporated by reference.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for forming an anti-microbial layer on an apparatus, comprising:
   (a) forming a titanium (Ti) vapor that solidifies to form a titanium (Ti) layer on the apparatus;
   (b) forming a titanium-nitride (TiN) vapor that coats the titanium (Ti) layer with a titanium-nitride (TiN) layer; and
   (c) reacting the titanium-nitride (TiN) layer with an allyl halide or an alkenyl halide to quaternize the titanium-nitride (TiN) to form a quaternized the titanium-nitride (TiN) wherein the apparatus is selected from the group consisting of a dental implant, a crown, a bridge, a filling, a veneer, an inlay, an onlay, an endodontic device, and an orthodontic bracket.

2. The method of claim 1, wherein the allyl halide is a C1-C6 alkyl halide.

3. The method of claim 1, wherein the allyl halide is a C1-C6 alkyl bromide.

4. The method of claim 3, wherein the C1-C6 alkyl bromide is an allyl bromide.

5. The method of claim 1, wherein the alkenyl halide is a C1-C6 alkenyl halide.

6. The method of claim 1, wherein the alkenyl halide is a C1-C6 alkenyl bromide.

7. The method of claim 6, wherein the C1-C6 alkenyl bromide is an alkenyl bromide.

8. The method of claim 1, wherein the quaternized the titanium-nitride (TiN) has a thickness of about 50 Å to about 1000 Å.

9. The method of claim 1, wherein the titanium layer has a thickness of about 100 Å to about 3000 Å.

10. The method of claim 1, wherein the quaternized the titanium-nitride (TiN) consists of the reaction product of the titanium-nitride (TiN) layer with the allyl halide or the alkenyl halide.

11. The method of claim 1, wherein the apparatus is the dental implant.

* * * * *